United States Patent [19]
Leduc et al.

[11] Patent Number: 6,027,537
[45] Date of Patent: Feb. 22, 2000

[54] USE OF SILICON COMPOUNDS TO DYE HUMAN KERATIN FIBRES; NOVEL COMPOUNDS AND COMPOSITIONS CONTAINING THEM

[75] Inventors: Madeleine Leduc, Paris; Hervé Richard, Villepinte; Alain Lagrange, Coupvray, all of France

[73] Assignee: L'Oreal, Paris, France

[21] Appl. No.: 08/961,261

[22] Filed: Oct. 30, 1997

[30] Foreign Application Priority Data

Oct. 30, 1996 [FR] France ................... 96 13267

[51] Int. Cl.$^7$ ............... C07F 7/18; C07F 7/10; A61K 7/13; C08G 77/14
[52] U.S. Cl. .................. 8/405; 8/425; 8/404; 8/609; 8/611; 8/647; 8/662; 8/663; 8/673; 8/675; 8/676; 8/677; 8/916; 8/DIG. 1; 8/428; 8/429; 8/435; 8/437; 534/726; 534/683; 556/413; 556/418; 556/419; 556/423; 556/425; 556/428; 556/436; 556/450; 556/453; 556/422; 544/69; 544/1; 548/110; 552/209
[58] Field of Search .............. 8/405, 425, 404, 8/609, 611, 647, 662, 663, 673, 675, 676, 677, 916, DIG. 1, 428, 429, 435, 437; 534/726, 683; 556/413, 418, 419, 423, 425, 428, 436, 450, 453, 422; 544/69, 1; 548/110; 552/209

[56] References Cited

U.S. PATENT DOCUMENTS

| | | |
|---|---|---|
| 2,931,693 | 4/1960 | Bailey et al. . |
| 3,429,646 | 2/1969 | Steed ............................ 8/405 |
| 4,038,293 | 7/1977 | Smith et al. . |
| 4,381,260 | 4/1983 | Chu et al. ................. 534/726 |
| 5,231,206 | 7/1993 | Spes et al. ................. 556/413 |
| 5,663,270 | 9/1997 | Richard et al. ............. 528/27 |

FOREIGN PATENT DOCUMENTS

| | | |
|---|---|---|
| 154020 | 4/1978 | Germany . |
| 882 063 | 11/1961 | United Kingdom . |
| 882063 | 11/1961 | United Kingdom . |

OTHER PUBLICATIONS

Hemzawi et al, Journal of the Society of Dyers and Colourists, "Dyes and Pigments Containing Organosilicon Functional Groups," vol. 85, No. 9, pp. 401–404, Sep. 1969.

Ingaki et al, Macromolecules, vol. 22, pp. 4641–4643 (month unknown), 1989.

Zhang et al, Chemical Journal of Chinese Universities, vol. 16, No. 9, pp. 1380–1384, Sep. 1995.

Dietrich et al, Ber. Bunsenges. Phys. Chem., vol. 100, No. 7, pp. 1128–1132 (month unknown), 1996.

Chemical Abstracts, vol. 75, No. 141953y, Dec. 1971.

Trotman, "Dyeing and Chemical Technology of Textile Fibres," 6th edition, pp. 437–438, 1984.

Chemical Abstracts, vol. 75, No. 141953y, Dec. 13, 1971.

Chemical Abstracts, vol. 123, No. 146685g, Sep. 18, 1995.

*Primary Examiner*—Alan Diamond
*Attorney, Agent, or Firm*—Finnegan, Henderson, Farabow, Garrett & Dunner, L.L.P.

[57] ABSTRACT

The use of linear or cyclic silicon compounds containing at least one chromophoric group of quinone or azo type as direct dyes in dye compositions intended for dyeing human keratin fibres and in particular the hair. The invention also relates to novel silicon compounds and dye compositions containing them, as well as to the corresponding direct dyeing process.

24 Claims, No Drawings

USE OF SILICON COMPOUNDS TO DYE HUMAN KERATIN FIBRES; NOVEL COMPOUNDS AND COMPOSITIONS CONTAINING THEM

The invention relates to the use of linear or cyclic silicon compounds containing at least one chromophoric group of quinone or azo type as direct dyes in a dye composition intended for dyeing human keratin fibres and in particular the hair; the invention also relates to some of these silicon compounds as novel compounds.

Silicon dyes have already been described and proposed for dyeing synthetic fibres; such dyes are described in Belgian patent Nos. 875,160, 875,182 and 875,230, U.S. Pat. No. 2,925,313, German patent No. 2,918,685 and in European patent application No. 455,595, the disclosures of which are specifically incorporated by reference herein.

Silicon dyes have also been described and proposed for dyeing silicone resins: see in this respect U.S. Pat. Nos. 3,888,891, 3,981,859 and 4,038,293, the disclosures of which are specifically incorporated by reference herein. Silicon dyes which can be used in the manufacture of photosensitive polymers are also known in the prior art: see German patent application No. 2,040,831, the disclosure of which is specifically incorporated by reference herein.

For most of them, these silicon dyes are reactive on account of hydrolysable groups carried in their structure, and they have never been proposed for use in cosmetics.

Moreover, certain unreactive but physically and chemically inert polysiloxane dyes of high molecular weight have been prepared, in the U.S. Pat. No. 4,381,260, the disclosure of which is specifically incorporated by reference herein, and proposed, on account of their stability, for uses such as the dyeing of natural textiles, of plastics, or for dyeing foodstuffs and pharmaceutical and cosmetic preparations.

However, in the field of hair dyeing, direct dyes are sought, that is to say dyes which, without supplying an oxidizing agent, are capable by themselves of temporarily modifying the natural shade of the hair. In this application, it is desired that the dyes satisfy a certain number of criteria; they will preferably be as inoffensive as possible, that is to say that they have an acceptable level of harmlessness, and they will preferably give rise to colorations that are sufficiently fast, in particular with respect to light, washing, perspiration and bad weather.

Among the direct dyes conventionally used in hair dyeing, quinone dyes such as those of anthraquinone, benzoquinone and naphthoquinone type and azo dyes are known. Not all of these dyes are entirely inoffensive, which is why, in hair cosmetics, dye molecules of this type with increasingly higher levels of performance in terms of harmlessness are sought.

Now, after considerable research conducted in this matter, the inventors have discovered that silicon compounds which contain at least one chromophoric group of quinone or azo type, and some of which are novel, make it possible to dye human keratin fibres such as the hair without an oxidizing agent, with the advantageous property of having an excellent level of harmlessness.

In addition, the hair colorations obtained using these compounds are faster than those produced with non-silicon compounds of quinone or azo type of the prior art.

This discovery forms the basis of the present invention.

The subject of the present invention is thus the use, as direct dyes in a dye composition intended for dyeing human keratin fibres and in particular the hair, of linear or cyclic silicon compounds containing at least one chromophoric group of quinone or azo type, characterized in that they correspond to one of the formulae (1), (2) or (3) below:

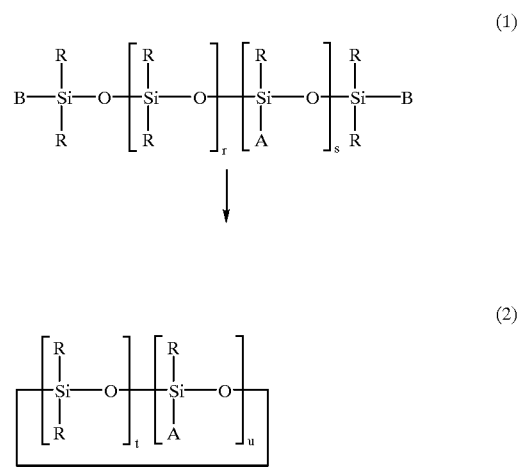

in which formulae (1) and (2):

R, which may be identical or different, are chosen from $C_1$–$C_{10}$ alkyl, phenyl and 3,3,3-trifluoropropyl radicals, at least 80%, in numerical terms, of the radicals R being methyl, B, which may be identical or different, are chosen from the above radicals R and the radical A defined below, r is an integer ranging from 0 to 50, and s is an integer ranging from 0 to 20, with the condition that if s is zero then at least one of the two symbols B denotes A, u is an integer ranging from 1 to 6, and t is an integer ranging from 0 to 10, it being understood that t+u is equal to or greater than 3,

in which formula (3):

$R_1$, $R_2$ and $R_3$, which may be identical or different, are chosen from linear or branched, saturated or unsaturated $C_1$–$C_8$ alkyl and alkenyl radicals, and in which formulae (1), (2) and (3) the symbol A denotes a radical, which may be identical or different, of formula (4a), (4b), (4c) or (4d) below:

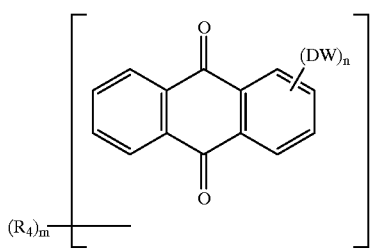

(4a)

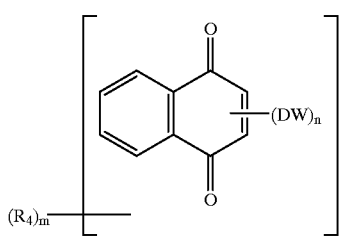

(4b)

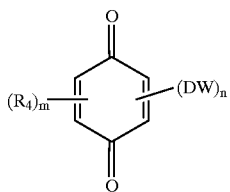

(4c)

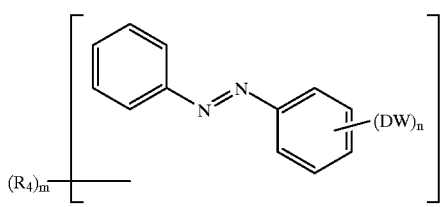

(4d)

in which formulae (4a), (4b), (4c) and (4d):

$R_4$, which may be identical or different, represent a linear or branched $C_1$–$C_6$ alkyl radical, OH, $C_1$–$C_4$ alkoxy, hydroxy($C_1$–$C_4$)alkyl, COOH, $CONH_2$, CN, $SO_3H$, a halogen, an $NO_2$ radical, or a radical $NR_5R_6$ in which $R_5$ and $R_6$, which may be identical or different, denote a hydrogen atom, a $C_1$–$C_8$ alkyl or hydroxy($C_1$–$C_4$)alkyl or amino($C_1$–$C_4$)alkyl radical, or form, together with the nitrogen atom to which they are attached, a 5- or 6-membered heterocycle which may be interrupted by an oxygen or sulphur atom, m is an integer ranging from 0 to 2, n is an integer equal to 1 or 2, D is an —$SO_2NH$—, —CONH— or —O— radical or a radical —$NR_7$— in which $R_7$ is H or $CH_3$, W is a divalent radical of formula (5):

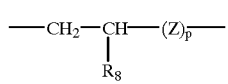

(5)

or of formula (6):

$$—HC=CH—(Z)_p— \quad (6)$$

in which formulae (5) and (6):

$R_8$ denotes a hydrogen atom, a hydroxyl radical or a linear or branched, saturated or unsaturated $C_1$–$C_8$ alkyl radical, Z is a linear or branched $C_1$–$C_6$ alkylene radical optionally substituted with an OH radical or a linear or branched, saturated or unsaturated $C_2$–$C_8$ alkoxy radical, and p is an integer equal to 0 or 1.

In formulae (1), (2) and (3) above, A thus represents a quinone (anthraquinone, naphthoquinone or benzoquinone) or azo group which, after attaching to the starting silicon chains, gives the compounds of formulae (1), (2) and (3) dyeing properties.

The alkyl radicals may be chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radicals R and B which are preferred according to the invention are the methyl, ethyl, propyl, n-butyl, n-octyl and 2-ethylhexyl radicals. Even more preferably, the radicals R and B are all methyl radicals.

Among the linear or cyclic silicon compounds which may be used according to the present invention, random derivatives or derivatives with well-defined blocks having at least one, and even more preferably all, of the following characteristics:

R is alkyl and even more preferably methyl,

B is alkyl and even more preferably methyl, r ranges from 0 to 3 and is more preferably zero, s ranges from 1 to 3, more preferably equal to 1, t+u ranges from 3 to 5, $R_1$, $R_2$ and $R_3$ are alkyl and even more preferably methyl, $R_8$ is hydrogen, Z is methylene and p is equal to 1, are more particularly preferred.

According to the invention, the compounds more particularly preferred are the following:

4-(4-dimethylaminophenylazo)-N-[3-[1,3,3,3-tetramethyl-1-[(trimethylsilyl)oxy]disiloxanyl]-propyl]benzenesulphonamide [compound (7)]:
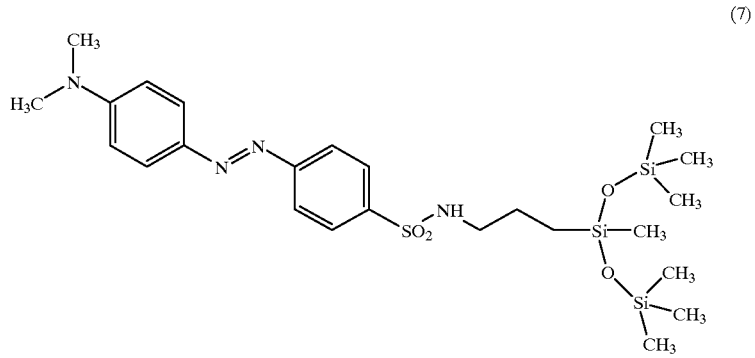
(7)
4-(4-dimethylaminophenylazo)-N-[3-[1,3,3,3-tetramethyl-1-[(trimethylsilyl)oxy]disiloxanyl]-propyl]benzamide [compound (8)]:
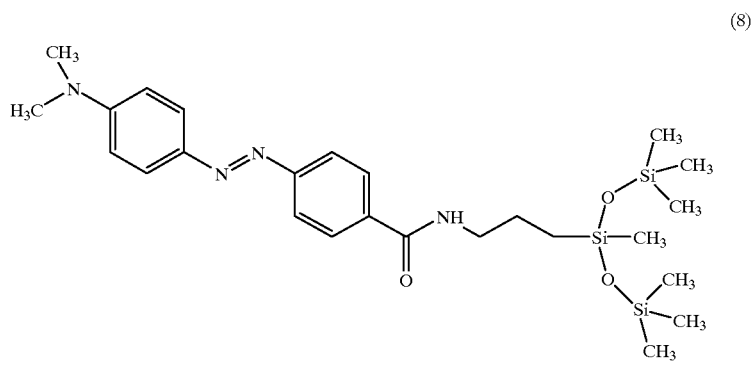
(8)
2-(4-methoxy-2-nitrophenylazo)-5-(3-trimethylsilanylpropoxy)phenol [compound (9)]:
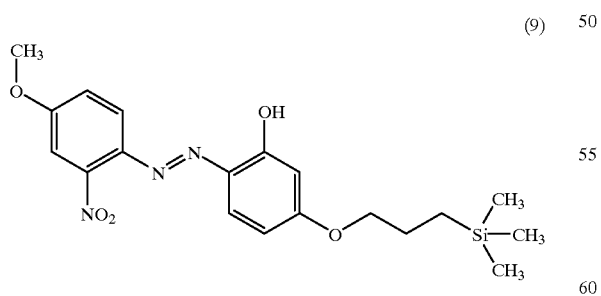
(9)

2,5-bis[3-[1,3,3,3-tetramethyl-1-[(trimethylsilyl)oxy] disiloxanyl]propylamino]benzoquinone [compound (10)]:

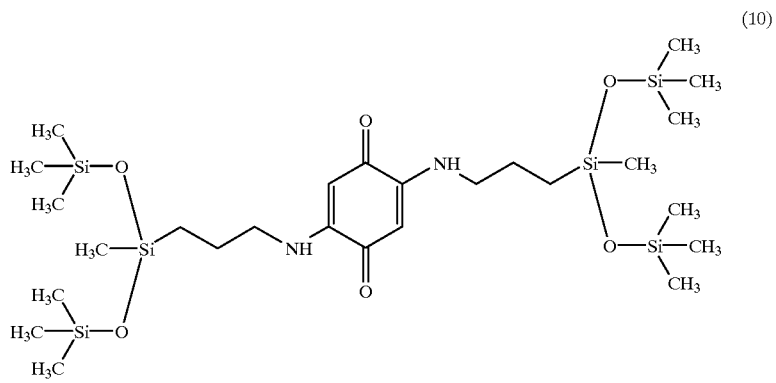

2-chloro-3-[3-[1,3,3,3-tetramethyl-1-[(trimethylsilyl)oxy] disiloxanyl]propylamino]-[1,4]-naphthoquinone [compound (11)]:

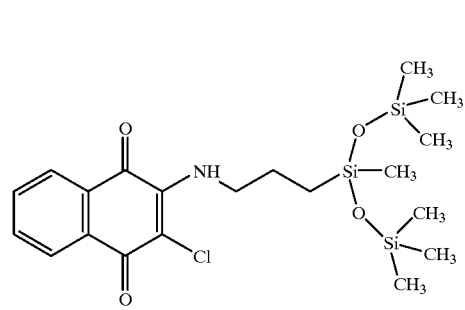

2-[3-[1,3,3,3-tetramethyl-1-[(trimethylsilyl)oxy] disiloxanyl]propylamino]-[1,4]-naphthoquinone [compound (12)]:

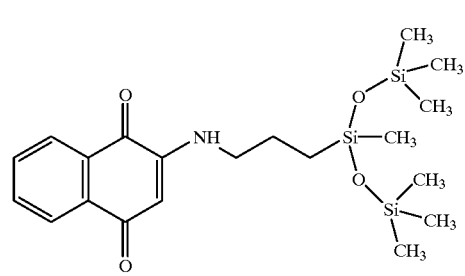

1-hydroxy-4-[3-[1,3,3,3-tetramethyl-1-[(trimethylsilyl)oxy]disiloxanyl]propylamino]-anthraquinone [compound (13)]:

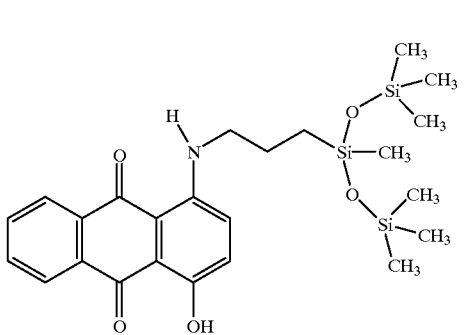

1,4-di-[3-[1,3,3,3-tetrammehyl-1-[(trimethylsilyl)oxy] disiloxanyl]propylamino]-anthraquinone [compound (14)]:

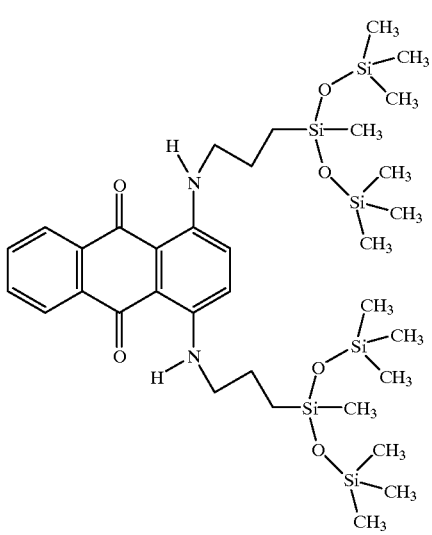

To prepare the silicon dyes of formulae (1), (2) and (3), it is possible to work conventionally (route 1), by carrying out a hydrosilylation reaction, namely:

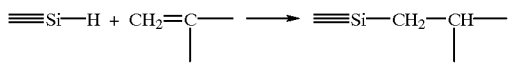

starting with the corresponding silicon compound, in which, for example, all the radicals A are hydrogen atoms. This starting silicon compound is referred to hereinbelow as the SiH derivative; the SiH groups may be present in the chain and/or at the ends of the silicon chain. These SiH derivatives are products that are well known in the silicone industry and are widely commercially available. They are described, for example, in U.S. Pat. Nos. 3,220,972, 3,697,473 and 4,340,709, the disclosures of which are specifically incorporated by reference herein.

This SiH derivative may thus be represented either by formula (15) below:

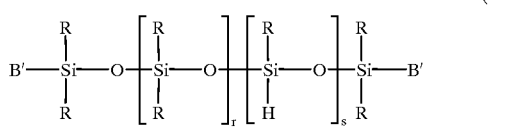

(15)

in which R, r and s have the meanings given above for formula (1) and the radicals B', which may be identical or different, are chosen from the radicals R and a hydrogen atom, or by formula (16) below:

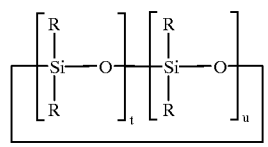

(16)

in which R, t and u have the meaning given above for formula (2), or by formula (17) below:

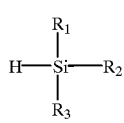

(17)

in which $R_1$, $R_2$ and $R_3$ have the meanings given above for formula (3).

A standard hydrosilylation reaction is thus carried out on this SiH derivative of formula (15), (16) or (17), in the presence of a catalytically effective amount of a platinum catalyst, on an organic compound of formula (4a), (4b), (4c) or (4d), in which the symbol W is replaced by the symbol (W') which denotes a monovalent radical of formula (18) or (19) below:

(18)

(19)

in which formulae (18) and (19), Z, $R_8$ and p have the same meanings as in formulae (5) and (6) defined above.

Another possible synthetic route (route 2) which is suitable for preparing silicon dyes of formulae (1), (2) and (3) comprises the step of reacting an aminosilicon compound corresponding to formula (15), (16) or (17) defined above, but in which the hydrogen atom has been replaced by a monovalent radical of formula: —D—$CH_2$—$CHR_8$—$(Z)_p$—$NH_2$, in which D has same meanings as in formulae (4a), (4b), (4c) and (4d) defined above and $R_8$ and p have the same meanings as in formulae (5), (6), (18) and (19) defined above, on a compound of formula (20a), (20b), (20c) or (20d) below:

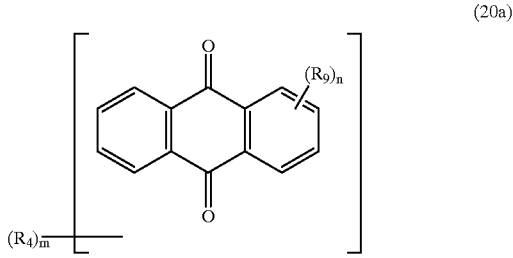

(20a)

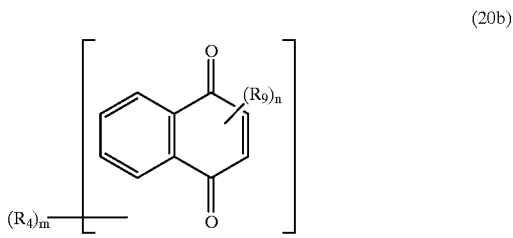

(20b)

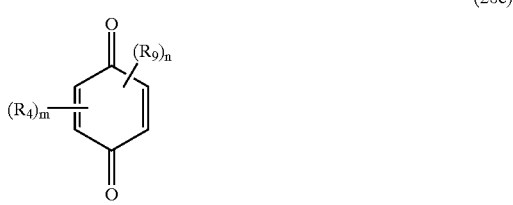

(20c)

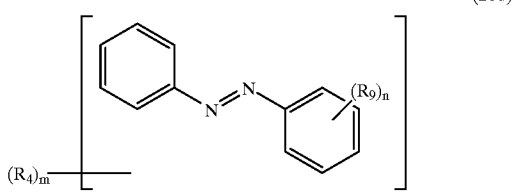

(20d)

in which formula (20a), (20b), (20c) or (20d):

$R_4$, m and n have the same meanings as in formulae (4a), (4b), (4c) and (4d) defined above, and $R_9$ denotes a hydrogen atom, a halogen atom or a hydroxyl radical.

Among the compounds of formula (1) of the invention, some are known per se, in particular those described in U.S. Pat. No. 4,381,260 and patent SU 1,712,374, the disclosures of which are specifically incorporated by reference herein.

Others are novel and constitute another subject of the present invention.

Another subject of the present invention is thus novel compounds of formula (1) defined below, and of formula (2) defined above.

The said novel compounds of formula (1) are those for which:
(i) the radicals B denote a $CH_3$ radical, s is equal to 1 and r denotes an integer ranging from 0 to 10, and
(ii) s denotes zero, the radicals B simultaneously denote a radical A of formula (4a), and D is other than NH.

The said compounds of formula (3) are novel except for those for which A is a group of formula (4d), $R_8$ denotes hydrogen, $R_1$, $R_2$ and $R_3$ denote alkyl groups and D denotes a group $NR_7$, which are described in GB patent 882,063 and U.S. Pat. No. 2,931,693, the disclosures of which are specifically incorporated by reference herein.

The subject of the invention is also a dye composition for human keratin fibres and in particular the hair, and more particularly a direct dye composition for hair, comprising, in a medium which is suitable for dyeing, an effective amount of at least one compound of formula (1), (2) or (3) defined above.

However, other characteristics, aspects and advantages of the invention will emerge even more clearly on reading the description which follows, as well as the various concrete, but in no way limiting, examples intended to illustrate it.

The compounds of formula (1), (2) or (3) are generally present in proportions ranging approximately from 0.01 to 10%, preferably approximately from 0.1 to 5%, by weight relative to the total weight of the dye composition.

The compounds of formula (1), (2) or (3) may also be incorporated into dye compositions for oxidation dyeing which contain oxidation bases and optionally couplers, in order to enrich with glints the shades obtained with the oxidation dyes.

The medium which is suitable for dyeing is, in this case, preferably a medium comprising water and/or cosmetically acceptable organic solvents, and more particularly alcohols (ethyl alcohol, isopropyl alcohol, benzyl alcohol and phenylethyl alcohol), glycols or glycol ethers (propylene glycol or ethers thereof such as, for example, propylene glycol monomethyl ether, butylene glycol and dipropylene glycol, as well as diethylene glycol alkyl ethers such as, for example, diethylene glycol monoethyl ether or monobutyl ether, and ethylene glycol monomethyl, monoethyl and monobutyl ethers), in concentrations ranging approximately from 0.5 to 20%, and preferably approximately from 2 to 10%, by weight relative to the total weight of the composition.

The said dye composition may also contain any other adjuvant commonly used in dyeing human keratin fibres and, for example, surfactants that are well known in the state of the art and of anionic, cationic, nonionic, amphoteric or zwitterionic type or mixtures thereof, thickeners, antioxidizing agents, fragrances, sequestering agents, dispersing agents, conditioners, preserving agents, opacifiers, etc.

Obviously, a person skilled in the art will take care to select the optionally additional compound(s) mentioned above such that the advantageous properties intrinsically associated with the dye composition according to the invention are not, or not substantially, adversely affected by the addition(s) envisaged.

The dye composition according to the invention may be formulated at acidic, neutral or alkaline pH, it being possible for the pH to range, for example, from 4 to 11 and preferably from 5 to 10, and it being possible for this pH to be adjusted using basifying or acidifying agents that were well known previously.

Among the basifying agents which may be mentioned, by way of example, are aqueous ammonia, alkaline carbonates, alkanolamines such as mono-, di- and triethanolamine as well as derivatives thereof, sodium hydroxide, potassium hydroxide and compounds of the following formula:

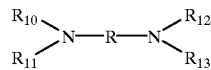

in which R is a propylene residue optionally substituted with a hydroxyl group or a $C_1$–$C_4$ alkyl radical, and $R_{10}$, $R_{11}$, $R_{12}$ and $R_{13}$, which may be identical or different, represent a hydrogen atom, a $C_1$–$C_4$ alkyl radical or a $C_1$–$C_4$ hydroxyalkyl radical. The acidifying agents are conventionally, by way of example, inorganic or organic acids such as hydrochloric acid, orthophosphoric acid, carboxylic acids such as tartaric acid, citric acid or lactic acid, or sulphonic acids.

The composition applied to the fibres may be in various forms, such as in the form of a liquid, a cream, a gel or any other form which is suitable for preparing a dye for keratin fibres. In particular, it may be packaged under pressure in an aerosol can in the presence of a propellant and may form a foam.

Another subject of the invention relates to a process for dyeing human keratin fibres, and in particular the hair, by direct dyeing, this process comprising the step of leaving a dye composition containing at least one compound of formula (1), (2) or (3) on the wet or dry keratin fibres. The composition according to the invention may be used as a leave-in composition, that is to say that after the composition has been applied to the fibres, they are dried without intermediate rinsing. In the other modes of application, the composition is left to act on the fibres for an exposure time ranging approximately from 3 to 60 minutes, preferably approximately from 5 to 45 minutes, after which the fibres are rinsed, optionally washed and rinsed again, and then dried.

Concrete examples illustrating the invention will now be given.

PREPARATION EXAMPLES

Example 1
Preparation of 4-(4-dimethylaminophenylazo)-N-[3-[1,3,3,3-tetramethyl-1-[(trimethylsilyl )oxy]-disiloxanyl]propyl] benzenesulphonamide:

(7)

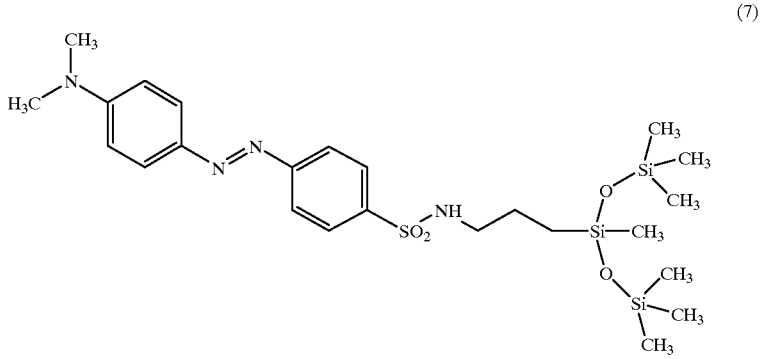

4-Dimethylamino-4'-azobenzenesulphonyl chloride (3.23 g, i.e. 0.01 mol) was added portionwise to a refluxing (40° C.) mixture of heptamethylamino-propyltrisiloxane (3.07 g, i.e. 0.011 mol), triethylamine (1.11 g, i.e. 0.011 mol) and dichloromethane (10 ml); the mixture was refluxed for 3 hours and then cooled. The reaction mixture was poured into 30 ml of water. The organic phase was washed with water and then dried over sodium sulphate. After recrystallization from methanol, compound (7) was obtained in the form of an orange-coloured powder.

m.p.: 82° C.
UV (ethanol) $\lambda_{max}$ = 432 nm, $\epsilon_{max}$ = 37350.
Elemental analysis for $C_{24}H_{42}N_4O_4SSi_3$

| | | | | | |
|---|---|---|---|---|---|
| theory: | C 50.85 | H 7.47 | N 9.88 | S 5.66 | Si 14.86 |
| found: | C 50.53 | H 7.54 | N 9.85 | S 5.51 | Si 14.90 |

Example 2
Preparation of 4-(4-dimethylaminophenylazo)-N-[3-1,3,3,3-tetramethyl-1-[(trimethylsilyl )oxy]-disiloxanyl]propyl] benzamide:

(8)

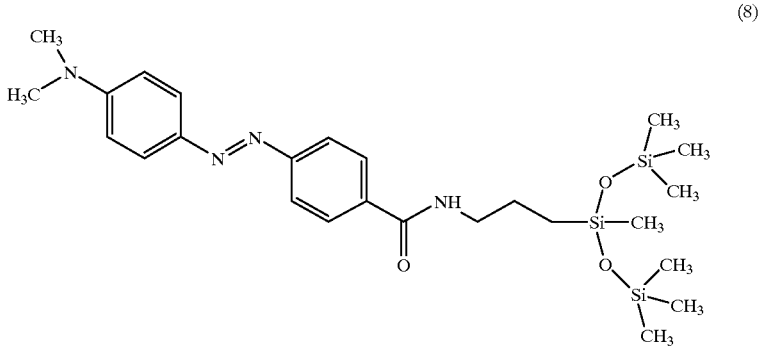

4-Dimethylaminoazobenzene-4'-carboxylic acid chloride (3.24 g, i.e. 0.01 mol) was added portionwise to a refluxing (40° C.) mixture of heptamethylamino-propyltrisiloxane (6.15 g, i.e. 0.022 mol), triethylamine (2.2 g, i.e. 0.022 mol) and dichloromethane (20 ml); the mixture was refluxed for 2 hours and then cooled. The reaction mixture was poured into 50 ml of water. The organic phase was washed with water and then dried over sodium sulphate. The crude product was purified by column chromatography (eluent: $CH_2Cl_2$). Compound (8) was thus obtained in the form of an orange-coloured powder.

m.p.: 187° C.
UV (ethanol) $\lambda_{max}$ = 428 nm, $\epsilon_{max}$ = 33500.
Elemental analysis for $C_{25}H_{42}N_4O_3Si_3$

| | | | | |
|---|---|---|---|---|
| theory: | C 56.56 | H 7.97 | N 10.55 | Si 15.87 |
| found: | C 56.32 | H 7.97 | N 10.47 | Si 16.10 |

Example 3
Preparation of 2-(4-methoxy-2-nitrophenylazo)-5-(3-trimethylsilanylpropoxy)phenol:

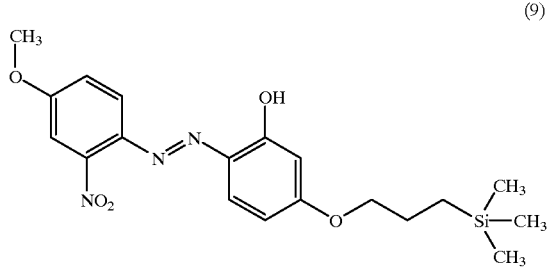

(9)

A mixture of 4-(4-methoxy-2-nitrophenylazo)benzene-1,3-diol (2.5 g, i.e. 0.0086 mol) and potassium carbonate (1.24 g) in 30 ml of dimethylformamide was brought to 70–75° C. 3-Chloropropyltrimethylsilane (1.24 g, i.e. 0.0086 mol) was added thereto over 20 minutes. The mixture was stirred at 75° C. for 6 hours. The reaction mixture was then poured into 50 ml of water and extracted with diisopropyl ether. The organic phase was dried, concentrated and purified by column chromatography (eluent: 50/50 heptane/$CH_2Cl_2$) to give compound (9) in the form of a red powder.

m.p.: 128–129° C.
UV (ethanol) $\lambda_{max}$ = 409 nm, $\epsilon_{max}$ = 21950.
Elemental analysis for $C_{19}H_{25}N_3O_5Si$

| | | | | |
|---|---|---|---|---|
| theory: | C 56.56 | H 6.24 | N 10.41 | Si 6.96 |
| found: | C 56.18 | H 6.12 | N 10.46 | Si 6.69 |

Example 4
Preparation of 2,5-bis[3-[1,3,3,3-tetramethyl-1-[(trimethylsilyl)oxy]disiloxanyl]propylamino]-benzoquinone:

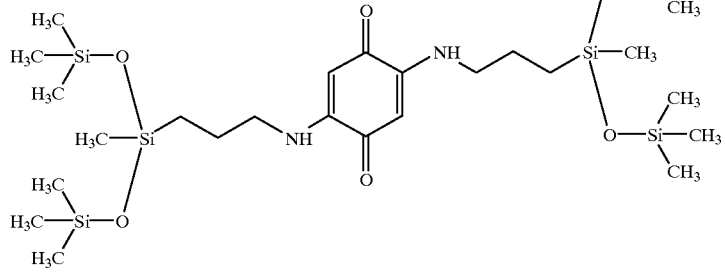

(10)

A mixture of benzoquinone (3.24 g, i.e. 0.03 mol), heptamethylaminopropyltrisiloxane (5.6 g, i.e. 0.02 mol) and ethanol (40 ml) was refluxed for 1 hour. The solvent was removed under vacuum and the residue was then taken up in 50 ml of heptane. The mixture was filtered to remove the hydroquinone formed and was purified by column chromatography (eluent: 50/50 heptane/$CH_2Cl_2$). Compound (10) was thus obtained in the form of a red powder.

m.p.: 124° C.
UV (ethanol) $\lambda_{max}$ = 341 nm, $\epsilon_{max}$ = 30095.
$\lambda_{max}$ = 494 nm, $\epsilon_{max}$ = 400.
Elemental analysis for $C_{26}H_{58}N_2O_6Si_6$

| | | | | |
|---|---|---|---|---|
| theory: | C 47.08 | H 8.81 | N 4.22 | Si 25.41 |
| found: | C 46.86 | H 8.76 | N 4.23 | Si 25.80 |

Example 5
Preparation of 2-chloro-3-[3-[1,3,3,3-tetramethyl-1-[(trimethylsilyl)oxy]disiloxanyl]propylamino]-[1,4]-naphthoquinone:

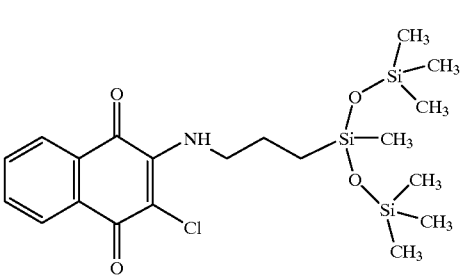

(11)

2.27 g, i.e. 0.01 mol, of 2,3-dichloronaphthoquinone in 30 ml of dichloromethane were brought to reflux. Heptamethylaminopropyltrisiloxane (11.2 g, 0.04 mol) was added thereto over 20 minutes and the mixture was refluxed for 1 hour. After concentration of the reaction medium, the solid formed was recrystallized from methanol. Compound (11) was obtained in the form of a red powder.

m.p.: 80–81° C.
UV (ethanol) $\lambda_{max}$ = 475 nm, $\epsilon_{max}$ = 3850.
Elemental analysis for $C_{20}H_{32}ClNO_4Si_3$

| | | | | | |
|---|---|---|---|---|---|
| theory: | C 51.09 | H 6.86 | Cl 7.54 | N 2.98 | Si 17.92 |
| found: | C 50.72 | H 6.89 | Cl 7.43 | N 3.12 | Si 18.28 |

Example 6
Preparation of 2-[3-[1,3,3,3-tetramethyl-1-[(trimethylsilyl)oxy]disiloxanyl]propylamino]-[1,4]-naphthoquinone:

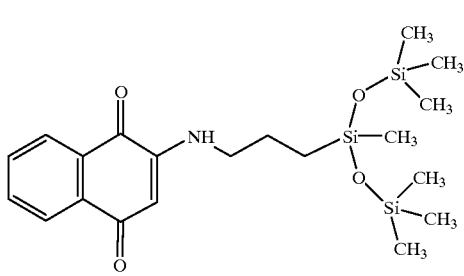

(12)

Naphthoquinone (4.74 g, i.e. 0.03 mol) and heptamethylaminopropyltrisiloxane (5.58 g, i.e. 0.02 mol) in ethanol (40 ml) were refluxed for 4 hours. After concentrating the reaction mixture to half its volume, the solid formed was isolated. Compound (13) was obtained in the form of an orange-coloured powder.

m.p.: 95–96° C.
UV (ethanol) $\lambda_{max}$ = 452 nm, $\epsilon_{max}$ = 3850.

Example 7
Preparation of 1-hydroxy-4-[3-[1,3,3,3-tetramethyl-1-[(trimethylsilyl)oxy]disiloxanyl]propylamino]-anthraquinone:

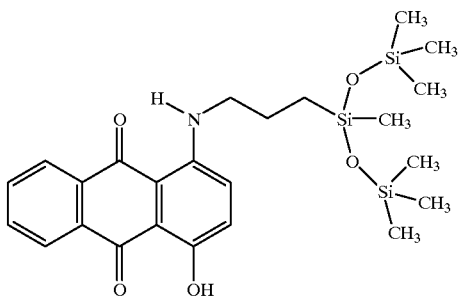

(13)

Leucoquinizarine (4.12 g, i.e. 0.017 mol) and heptamethylaminopropyltrisiloxane (11.88 g, i.e. 0.0425 mol) in tetrahydrofuran (40 ml) were refluxed for 3 hours. After cooling, a stream of air was bubbled through the reaction mixture for 2 hours. After column chromatography (eluent: 50/50 heptane/$CH_2Cl_2$), a mixture of compounds (13) and (14) was obtained. By crystallization of this mixture from 60 ml of methanol, compound (13) was recovered in the form of a violet powder.

m.p.: 71–72° C.
UV (ethanol)  $\lambda_{max}$ = 557 nm, $\epsilon_{max}$ = 13100.
  $\lambda_{max}$ = 598 nm, $\epsilon_{max}$ = 12400.
Elemental analysis for $C_{24}H_{35}NO_5Si_3$
theory:  C 57.45  H 7.03  N 2.79  Si 16.79
found:   C 57.44  H 7.04  N 2.80  Si 16.50

Example 8
Preparation of 1,4-bis[3-[1,3,3,3-tetramethyl-1-[(trimethylsilyl)oxy]disiloxanyl]propylamino]-anthraquinone:

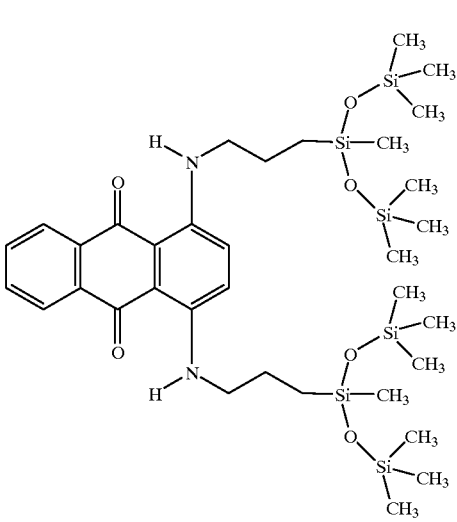

(14)

Leucoquinizarine (2.43 g, i.e. 0.01 mol) and heptamethylaminopropyltrisiloxane (8.37 g, i.e. 0.03 mol) in a mixture of toluene (50 ml) and N-methylpyrrolidone (20 ml) were refluxed for 2 hours. After cooling, a stream of air was bubbled through the reaction mixture for 2 hours. The reaction mixture was poured into water and the organic phase was washed with water. After column chromatography (eluent: 50/50 heptane/$CH_2Cl_2$), a mixture of compounds (13) and (14) was obtained. By crystallization of this mixture from 60 ml of methanol, compound (14) was recovered in the form of a deep-blue powder.

m.p.: 59–60° C.
UV (ethanol)  $\lambda_{max}$ = 595 nm, $\epsilon_{max}$ = 16950.
  $\lambda_{max}$ = 645 nm, $\epsilon_{max}$ = 20100.
Elemental analysis for $C_{34}H_{62}N_2O_6Si_6$
theory:  C 53.49  H 8.19  N 3.67  Si 22.07
found:   C 53.29  H 8.08  N 3.65  Si 22.10

EXAMPLES OF DYE COMPOSITIONS

Example 9

Locks of natural grey hair containing 90% white hairs were dyed with a dye composition containing $5 \times 10^{-2}$ mol of the dye prepared in Example 5, in an amount of a mixture of ethanol and water (90/10 by weight) which was sufficient to make the composition up to 100 g.

After treatment for 30 minutes, the hair was rinsed with water for 5 minutes and then dried.

The locks of hair were dyed orange-red.

Example 10

Locks of natural grey hair containing 90% white hairs were dyed with a dye composition containing $5 \times 10^{-2}$ mol of the dye prepared in Example 7, in an amount of a mixture of ethanol and water (90/10 by weight) which was sufficient to make the composition up to 100 g.

After treatment for 30 minutes, the hair was rinsed with water for minutes and then dried.

The locks of hair were dyed violet-red.

We claim:

1. A dye composition for human keratin fibres, comprising at least one compound of formula (1) or a salt thereof in a medium which is suitable for dyeing:

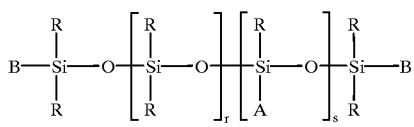
(1)

wherein:

each R is independently selected from $C_1$–$C_{10}$ alkyl, phenyl and 3,3,3-trifluoropropyl radicals, at least 80%, in numerical terms, of the radicals R being methyl, each B is independently selected from the above radicals R and the radical A defined below, r is an integer ranging from 0 to 50, and s is an integer ranging from 0 to 20, with the condition that if s is zero then at least one of the two symbols B denotes A, and each A denotes a radical independently selected from the group consisting of formula (4a), (4b), (4c) and (4d) below:

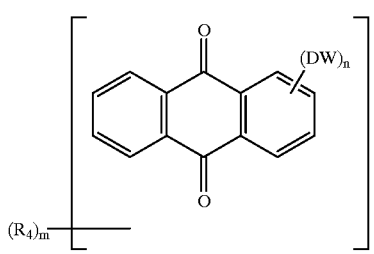
(4a)

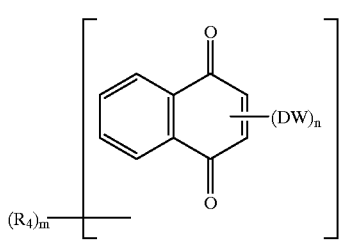
(4b)

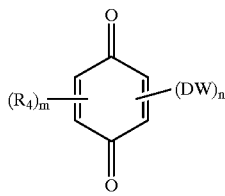
(4c)

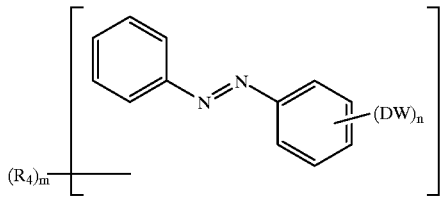
(4d)

wherein:

each $R_4$ independently represents a linear or branched $C_1$–$C_6$ alkyl radical, OH, $C_1$–$C_4$ alkoxy, hydroxy($C_1$–$C_4$)alkyl, COOH, $CONH_2$, CN, $SO_3H$, a halogen, an $NO_2$ radical, or a radical $NR_5R_6$, wherein $R_5$ and $R_6$ independently denote a hydrogen atom, a $C_1$–$C_8$ alkyl or hydroxy($C_1$–$C_4$)alkyl or amino($C_1$–$C_4$)alkyl radical, or form, together with the nitrogen atom to which they are attached, a 5- or 6-membered heterocycle which is interrupted by an oxygen or sulphur atom, m is an integer ranging from 0 to 2, n is an integer equal to 1 or 2, D is an —$SO_2NH$—, —CONH— or —O— radical or a radical —$NR_7$— wherein $R_7$ is H or $CH_3$, and W is a divalent radical of formula (5):

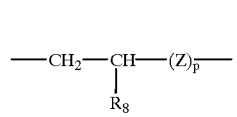
(5)

or of formula (6):

(6)

wherein:

$R_8$ denotes a hydrogen atom, a hydroxyl radical or a linear or branched, saturated or unsaturated $C_1$–$C_8$ alkyl radical, Z is a linear or branched $C_1$–$C_6$ alkylene radical optionally substituted with an OH radical or a linear or branched, saturated or unsaturated $C_2$–$C_8$ alkoxy radical, and p is an integer equal to 0 or 1, with the proviso that in formula (1), when:

(i) the radicals B denote a $CH_3$ radical, s is equal to 1 and r denotes an integer ranging from 0 to 10, and (ii) s denotes zero and the radicals B simultaneously denote the radical A of formula (4a), D is then other than NH.

2. A composition according to claim 1, wherein said human keratin fibres are hair.

3. A composition according to claim 1, wherein R is selected from methyl, ethyl, propyl, n-butyl, n-octyl and 2-ethylhexyl radicals.

4. A composition according to claim 3, wherein R is a methyl radical.

5. A composition according to claim 1, wherein B is selected from methyl, ethyl, propyl, n-butyl, n-octyl and 2-ethylhexyl radicals.

6. A composition according to claim 5, wherein B is a methyl radical.

7. A composition according to claim 1, wherein r ranges from 0 to 3, and s ranges from 1 to 3.

8. A composition according to claim 7, wherein r is equal to zero, and s is equal to 1.

9. A composition according to claim 1, wherein $R_8$ is hydrogen, Z is methylene, and p is equal to 1.

10. A composition according to claim 1, wherein at least one compound of formula (1) or a salt thereof is present in an amount effective to act as a direct dye.

11. A composition according to claim 1, wherein said composition has a pH ranging from 4 to 11.

12. A composition according to claim 1, wherein at least one compound of formula (1) is present in a concentration approximately ranging from 0.01 to 10% by weight relative to the total weight of the composition.

13. A composition according to claim 1, wherein said medium which is suitable for dyeing comprises water and/or organic solvents in proportions ranging from 0.5 to 20% by weight relative to the total weight of the composition.

14. A composition according to claim 13, wherein said organic solvents are selected from alcohols, glycols and glycol ethers.

15. A dye composition for human keratin fibres, comprising at least one of the following compounds or salts thereof in a medium which is suitable for dyeing:

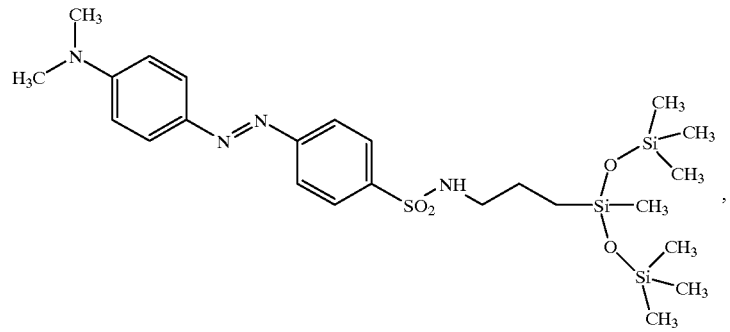

(7)

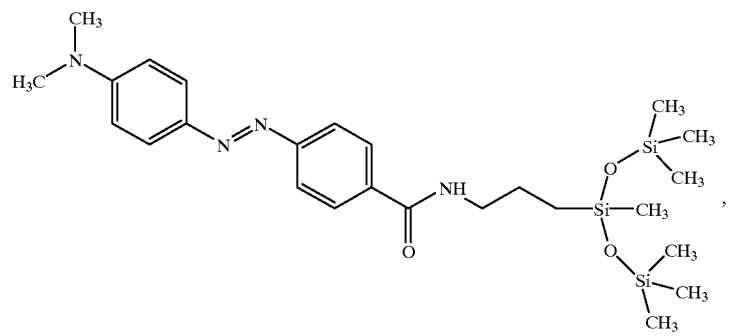

(8)

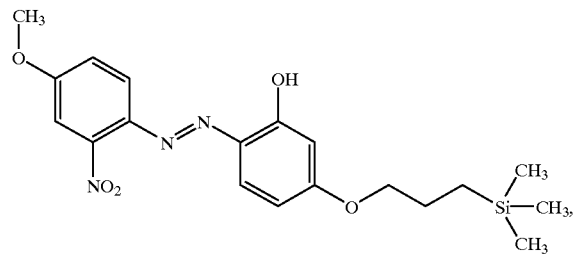

(9)

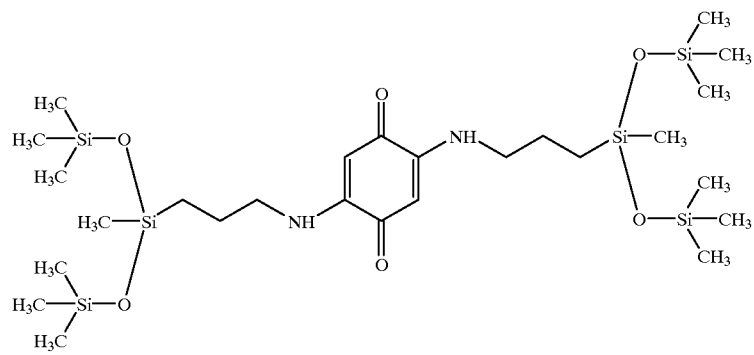

(10)

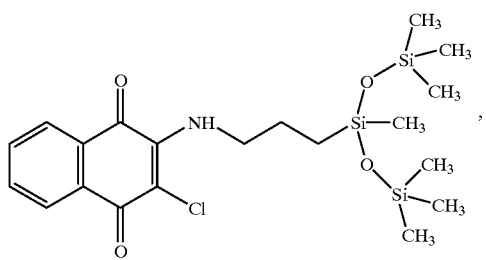
(11)
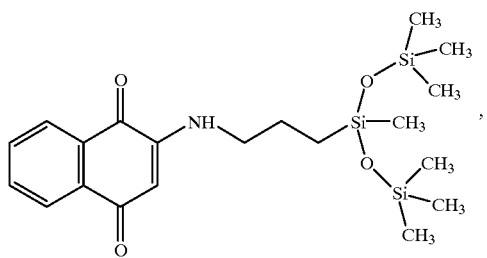
(12)
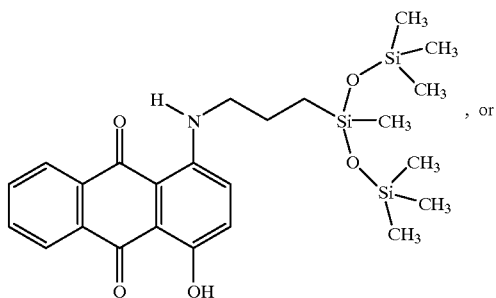
(13)
, or
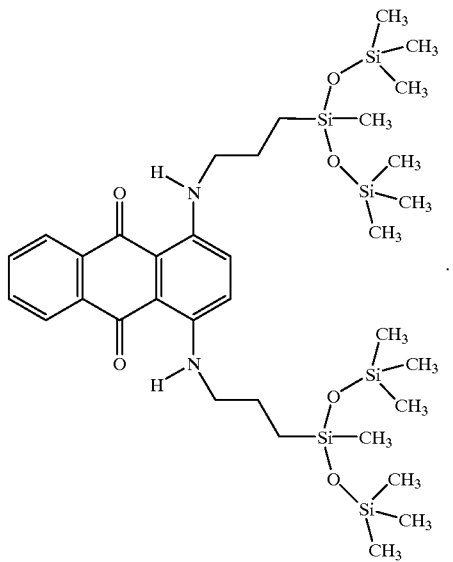
(14)

16. A compound of formula (1) or a salt thereof:

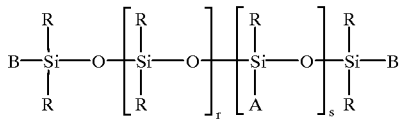
(1)

wherein:

each R [, which may be identical or different, are] is independently selected from $C_1$–$C_{10}$ alkyl, phenyl and 3,3,3-trifluoropropyl radicals, at least 80%, in numerical terms, of the radicals R being methyl, each B, [, which may be identical or different, are] is independently selected from the above radicals R and the radical A defined below, r is an integer ranging from 0 to 50, and s is an integer ranging from 0 to 20, with the condition that if s is zero then at least one of the two symbols B denotes A, and each A denotes a radical [, which may be identical or different, of] independently selected from the group consisting of formula (4a), (4b), (4c) and (4d) below:

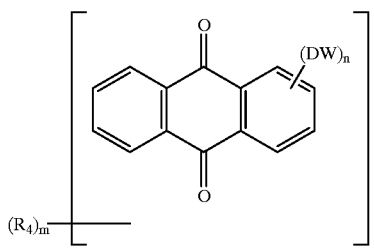
(4a)

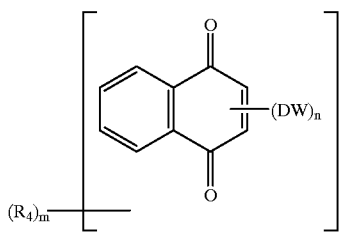
(4b)

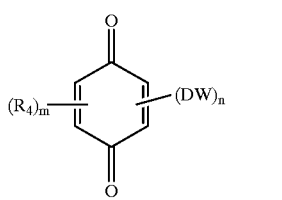
(4c)

-continued

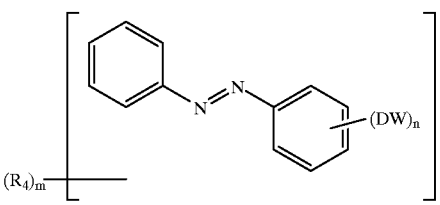
(4d)

wherein:

each $R_4$ [, which may be identical or different,] independently represents a linear or branched $C_1$–$C_6$ alkyl radical, OH, $C_1$–$C_4$ alkoxy, hydroxy($C_1$–$C_4$)alkyl, COOH, $CONH_2$, CN, $SO_3H$, a halogen, an $NO_2$ radical, or a radical $NR_5R_6$, wherein $R_5$ and $R_6$ [, which may be identical or different,] independently denote a hydrogen atom, a $C_1$–$C_8$ alkyl or hydroxy($C_1$–$C_4$)alkyl or amino($C_1$–$C_4$)alkyl radical, or form, together with the nitrogen atom to which they are attached, a 5- or 6-membered heterocycle which is interrupted by an oxygen or sulphur atom, m is an integer ranging from 0 to 2, n is an integer equal to 1 or 2, -D is an —$SO_2NH$—, —CONH— or —O— radical or a radical —$NR_7$— wherein $R_7$ is H or $CH_3$, and W is a divalent radical of formula (5):

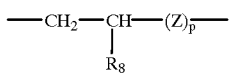
(5)

or of formula (6):

(6)

wherein:

$R_8$ denotes a hydrogen atom, a hydroxyl radical or a linear or branched, saturated or unsaturated $C_1$–$C_8$ alkyl radical, Z is a linear or branched $C_1$–$C_6$ alkylene radical optionally substituted with an OH radical or a linear or branched, saturated or unsaturated $C_2$–$C_8$ alkoxy radical, and p is an integer equal to 0 or 1, and with the proviso that, when:

(i) the radicals B denote a $CH_3$ radical, s is equal to 1 and r denotes an integer ranging from 0 to 10, and (ii) s denotes zero and the radicals B simultaneously denote the radical A of formula (4a), D is then other than NH.

17. A compound of the following formulae:
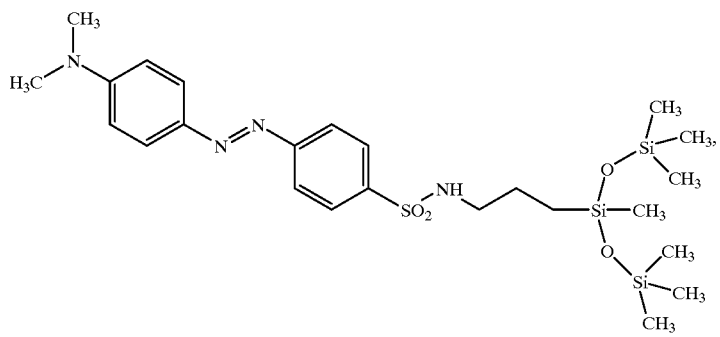
(7)
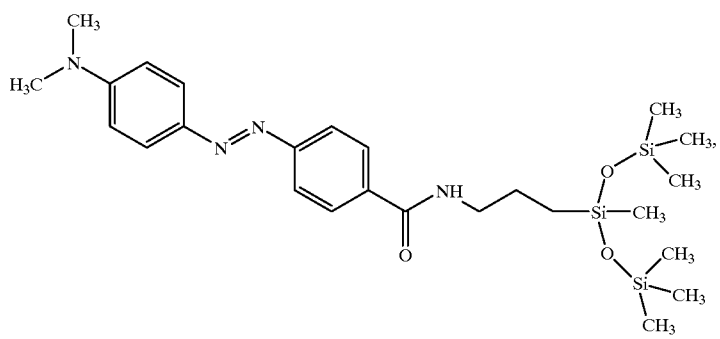
(8)
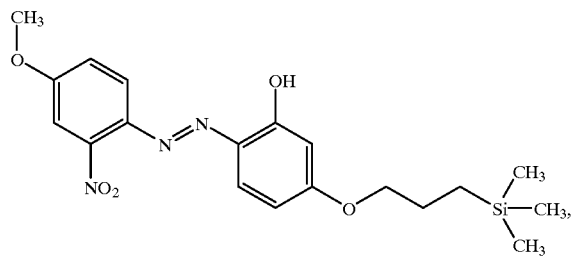
(9)
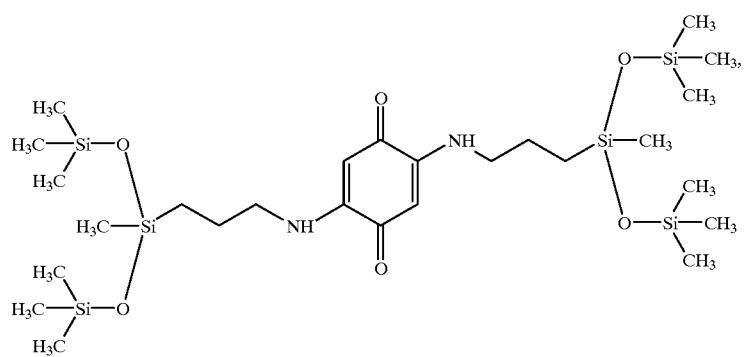
(10)

(11)
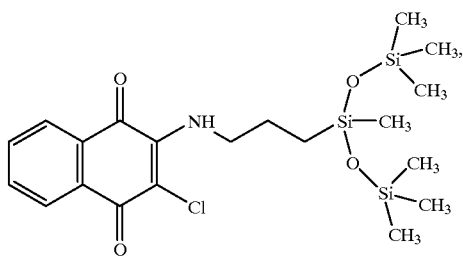
(12)
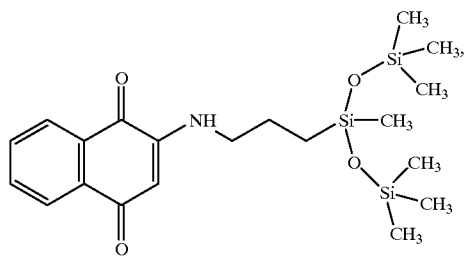
(13)
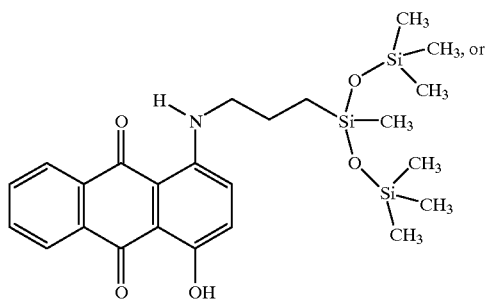
(14)
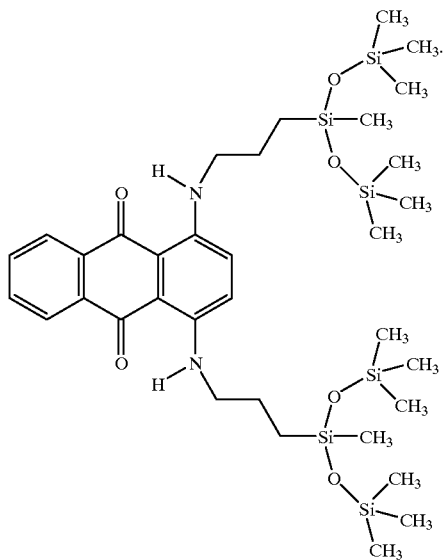

18. A process for the dyeing of human keratin fibres, comprising the step of applying to said fibres a dye composition comprising at least one compound of formula (1) or a salt thereof in a medium which is suitable for dyeing:

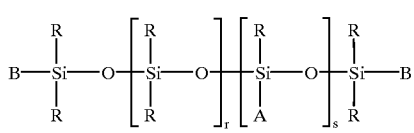

wherein:

each R is independently selected from $C_1$–$C_{10}$ alkyl, phenyl and 3,3,3-trifluoropropyl radicals, at least 80%, in numerical terms, of the radicals R being methyl, each B is independently selected from the above radicals R and the radical A defined below, r is an integer ranging from 0 to 50, and s is an integer ranging from 0 to 20, with the condition that if s is zero then at least one of the two symbols B denotes A, and each A denotes a radical independently selected from the group consisting of formula (4a), (4b), (4c) and (4d) below:

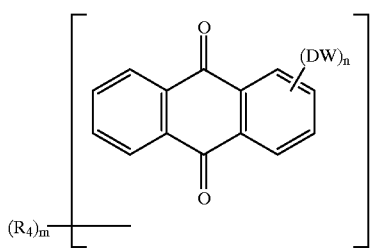

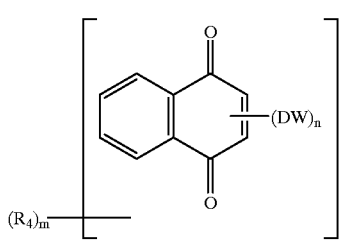

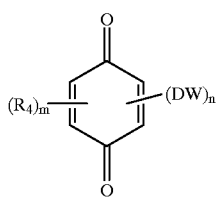

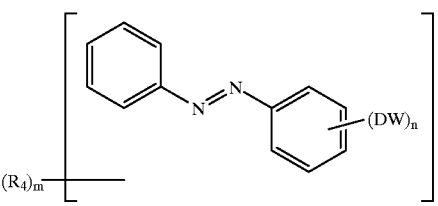

wherein:
each $R_4$ independently represents a linear or branched $C_1$–$C_6$ alkyl radical, OH, $C_1$–$C_4$ alkoxy, hydroxy($C_1$–$C_4$)alkyl, COOH, $CONH_2$, CN, $SO_3H$, a halogen, an $NO_2$ radical, or a radical $NR_5R_6$, wherein $R_5$ and $R_6$ independently denote a hydrogen atom, a $C_1$–$C_8$ alkyl or hydroxy($C_1$–$C_4$)alkyl or amino($C_1$–$C4$)alkyl radical, or form, together with the nitrogen atom to which they are attached, a 5- or 6-membered heterocycle which is interrupted by an oxygen or sulphur atom, m is an integer ranging from 0 to 2, n is an integer equal to 1 or 2, D is an —$SO_2NH$—, —CONH— or —O— radical or a radical —$NR_7$— wherein $R_7$ is H or $CH_3$, and W is a divalent radical of formula (5):

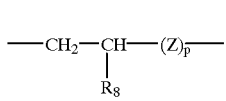

or of formula (6):

wherein:
$R_8$ denotes a hydrogen atom a hydroxyl radical or a linear or branched, saturated or unsaturated $C_1$–$C_8$ alkyl radical, Z is a linear or branched $C_1$–$C_6$ alkylene radical optionally substituted with an OH radical or a linear or branched, saturated or unsaturated $C_2$–$C_8$ alkoxy radical, and p is an integer equal to 0 or 1.

with the proviso that in formula (1), when:
(i) the radicals B denote a $CH_3$ radical, s is equal to 1 and r denotes an integer ranging from 0 to 10, and
(ii) s denotes zero and the radicals B simultaneously denote the radical A of formula (4a), D is then other than NH.

19. A process according to claim 18, wherein said human keratin fibres are hair.

20. A process according to claim 18, wherein said dye composition is applied to wet or dry keratin fibres and, after said composition has optionally been left on said fibres for an exposure time ranging from 3 to 60 minutes, said fibres are dried, after an optional rinsing operation.

21. A process for the direct dyeing of human keratin fibres, comprising the step of applying to said fibres a direct dye composition according to claim 10.

22. A process according to claim 21 wherein said human keratin fibres are hair.

23. A process according to claim 21 wherein said direct dye composition is applied to wet or dry keratin fibres and, after said composition has optionally been left on said fibres for an exposure time ranging from 3 to 60 minutes, said fibres are dried, after an optional rinsing operation.

24. A process for the dyeing of human keratin fibres, comprising the step of applying to said fibres a dye composition comprising at least one compound of the following formula:

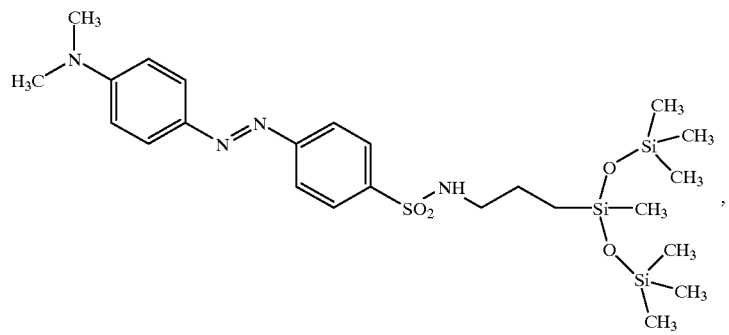
(7)

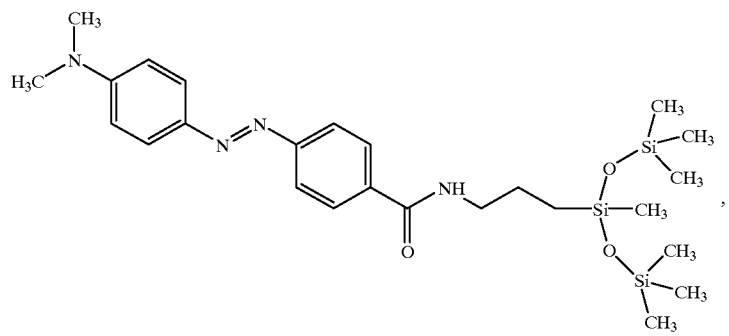
(8)

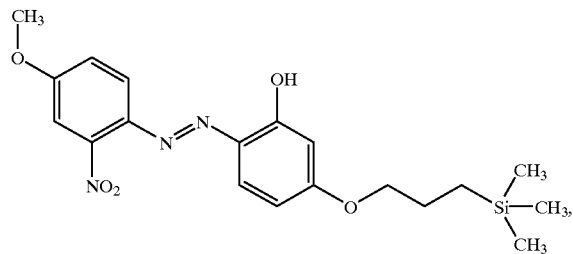
(9)

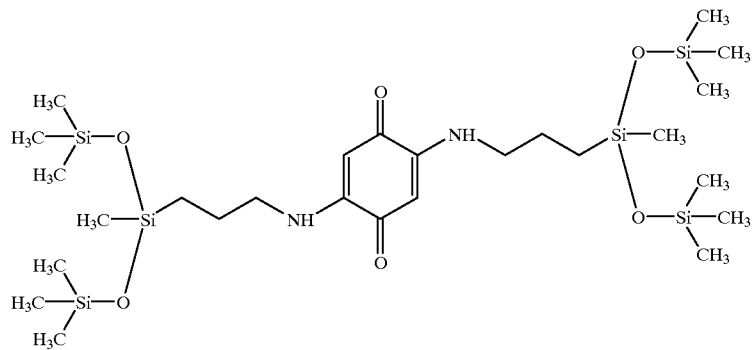
(10)

(11)
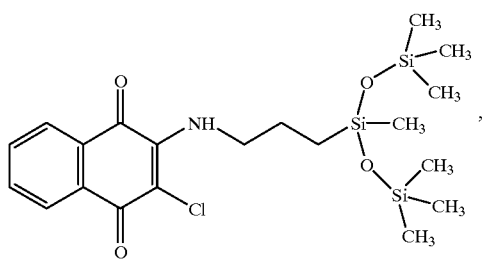,
(12)
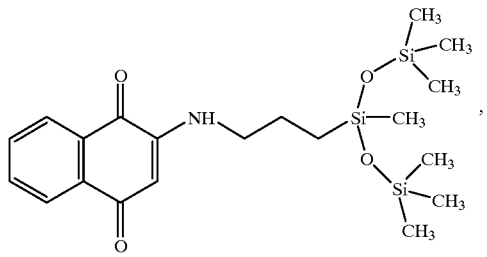,
(13)
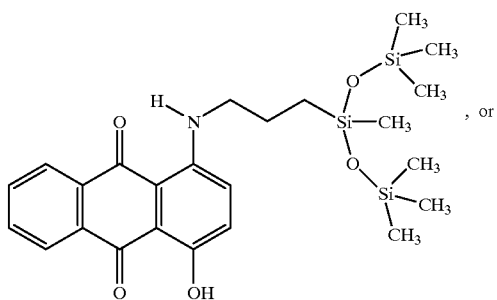, or
(14)
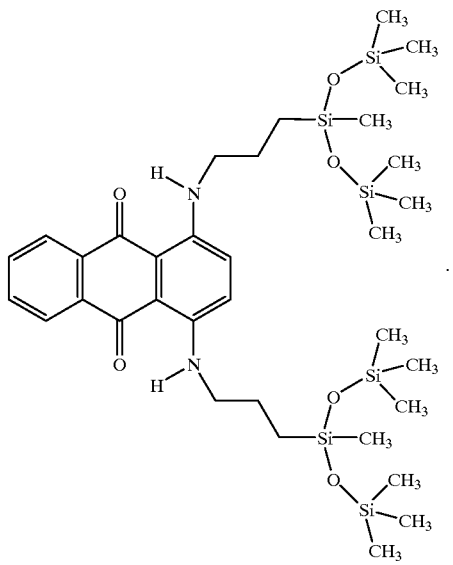.
* * * * *

UNITED STATES PATENT AND TRADEMARK OFFICE
CERTIFICATE OF CORRECTION

PATENT NO. : 6,027,537  
DATED : February 22, 2000  
INVENTOR(S) : Madeleine Leduc et al.

Page 1 of 1

It is certified that error appears in the above-identified patent and that said Letters Patent is hereby corrected as shown below:

Claim 16, Column 25,
Lines 16, 20, delete "[, which may be identical or different, are]".
Lines 30-31 delete "[, which may be identical or different, of]".

Claim 16, Column 26,
Lines 15, 21, delete "[, which may be identical or different,]".

Claim 21, Column 32,
Line 66, change "a direct" to -- the --.

Claim 23, Column 33,
Line 3, delete "direct".

Signed and Sealed this

Fourth Day of September, 2001

*Attest:*

*Attesting Officer*

NICHOLAS P. GODICI
*Acting Director of the United States Patent and Trademark Office*